United States Patent [19]

Cruz

[11] Patent Number: 4,935,004
[45] Date of Patent: Jun. 19, 1990

[54] PERITONEAL DIALYSIS CATHETER

[75] Inventor: Cosme Cruz, Grosse Pointe Farms, Mich.

[73] Assignee: Henry Ford Health System, Detroit, Mich.

[21] Appl. No.: 359,969

[22] Filed: May 31, 1989

Related U.S. Application Data

[63] Continuation-in-part of Ser. No. 286,974, Dec. 20, 1988, abandoned.

[51] Int. Cl.$^5$ ............................................. A61M 25/00
[52] U.S. Cl. ..................................... 604/29; 604/175; 604/281
[58] Field of Search ................... 604/27, 29, 175, 264, 604/280, 281

[56] References Cited

U.S. PATENT DOCUMENTS

| | | | |
|---|---|---|---|
| 4,027,659 | 6/1977 | Slingluff | 604/280 |
| 4,392,855 | 7/1983 | Oreopoulos | 604/29 |
| 4,681,564 | 7/1987 | Landreneau | 604/29 |
| 4,687,471 | 8/1987 | Twardowski et al. | 604/29 |
| 4,772,269 | 9/1988 | Twardowski et al. | 604/29 |

FOREIGN PATENT DOCUMENTS 0102342  3/1984  European Pat. Off. .............. 604/29

OTHER PUBLICATIONS

Palmer et al., "Prolonged Peritoneal Dialysis for Chronic Renal Failure", *The Lancet*, Mar. 28, 1964, pp. 700–702.

Primary Examiner—Stephen C. Pellegrino
Assistant Examiner—Ralph Lewis
Attorney, Agent, or Firm—Wallenstein, Wagner & Hattis, Ltd.

[57] ABSTRACT

A unique catheter for percutaneous access of the peritoneal cavity, such as in peritoneal dialysis, comprising a flexible tubular member having a distal portion being caudally disposed with the periotoneal cavity and a proximal portion passing through subcutaneous and cutaneous tissues and extending externally downward along the abdominal wall. Distal and proximal portions are each angularly joined to a linear connecting portion which is substantially disposed only through the rectus muscle. The connecting portion having a length generally co-extensive with the thickness of the rectus muscle. Porous cuff means for tissue ingrowth being carried on at least the connecting portion and preferably extending the length of the connecting portion. The distal and proximal portions of the catheter being non-planar with each other.

8 Claims, 2 Drawing Sheets

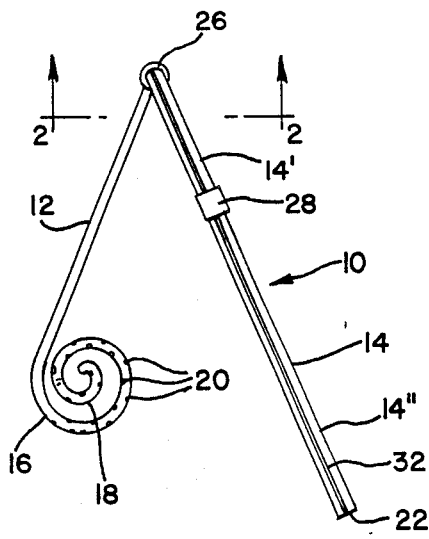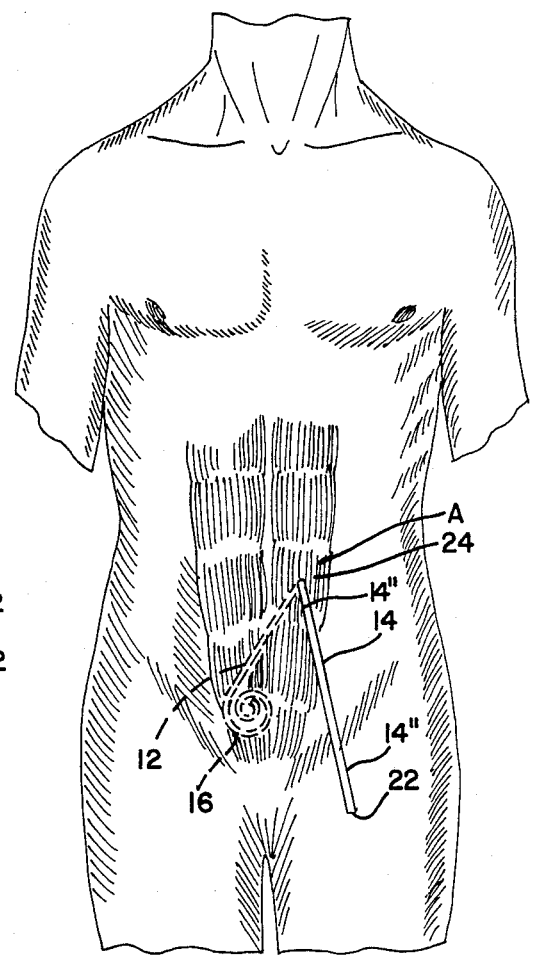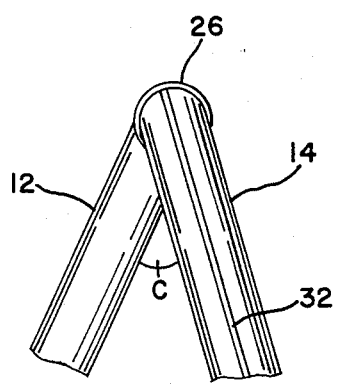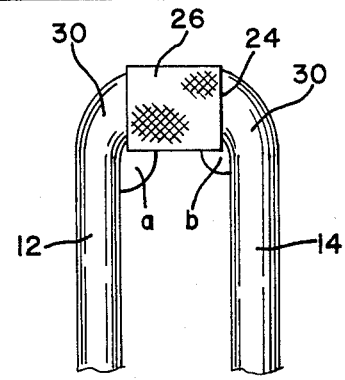

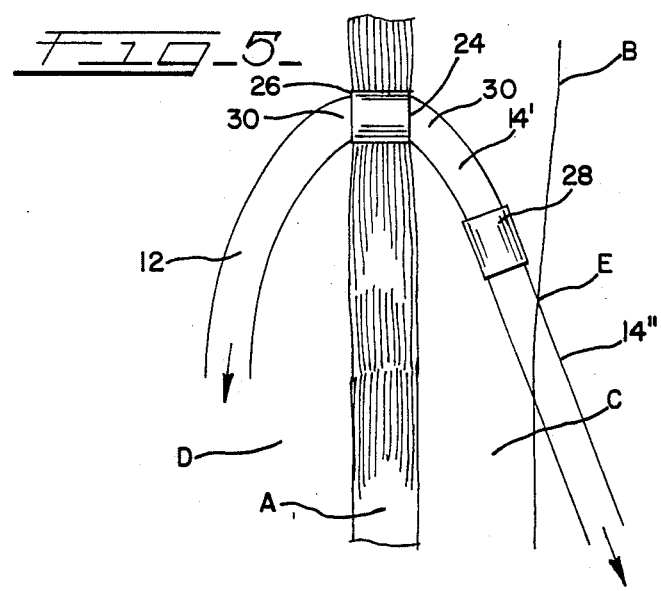
FIG-5-
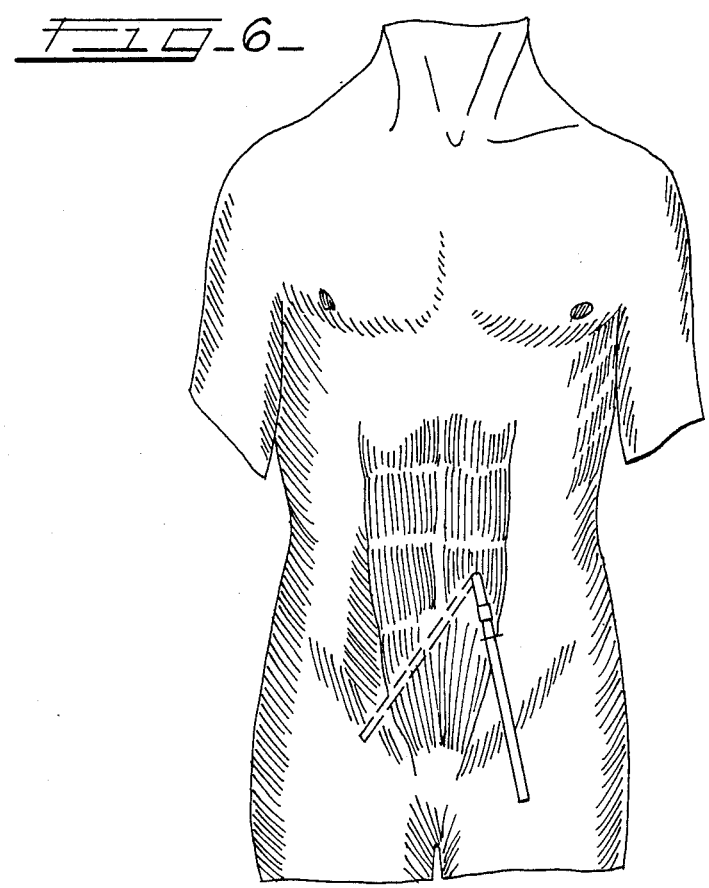
FIG-6-

PERITONEAL DIALYSIS CATHETER

REFERENCE TO RELATED APPLICATION

This is a continuation in part of application Serial No. 286,974, filed Dec. 20, 1988, now abandoned.

TECHNICAL FIELD OF THE INVENTION

The present application generally relates to catheters used to access the peritoneal cavity, and, in particular, to an improved peritoneal dialysis catheter.

BACKGROUND OF THE INVENTION

In the treatment of various diseases, percutaneous access to the peritoneal cavity is necessary. An example is peritoneal dialysis which is often indicated for acute or chronic renal failure. To effect dialysis through the peritoneal cavity, a percutaneous passage is surgically formed through the cutaneous and subcutaneous tissues, rectus muscle and through the peritoneum itself. This passage permits insertion and implantation of a distal portion of the catheter within the peritoneal cavity. A separate caudally directed tunnel is then formed through the subcutaneous and cutaneous tissues with a tunnel exit site in the suprapubic region of the external abdominal wall. A proximal portion of the catheter is inserted into the tunnel thereby maintaining an end of the proximal portion in a downward direction along the abdominal wall. Examples of catheters used in peritoneal dialysis are disclosed in U.S. Pats. Nos. 3,633,585; 4,184,497; 4,278,092; 4,279,252; 4,392,855; 4,687,471 and 4,772,269.

A significant problem with peritoneal dialysis catheters is the risk of post-operative infection, typically infection of the tunnel and of the tunnel exit site. The prior art has attempted to address this problem by use of "swan neck" catheters which are disclosed in U.S. Pats. No. 4,687,471 and 4,772,269. (Twardowski '471 and Twardowski '269, respectively). In swan neck catheters, the distal and proximal portions of the catheter are joined by an arcuately bend segment which caudally directs the distal portion of the catheter within the peritoneal cavity and downwardly directs the proximal portion of the catheter along the external abdominal wall. By caudally directing distal and proximal portions, it is suggested that tunnel infection and tunnel exit site infection is reduced. Twardowski '269 discloses that the bend segment defines an arc range of 100° to 180° and that such bend segment be permanently molded into the catheter so that it is maintained when the catheter is in a natural unstressed condition. Twardowski '269 suggests that such molded bend segment minimizes upward migration of the distal end portion of the catheter in the peritoneal cavity caused by the elastic memory of linear catheters having no molded bend segments.

Notwithstanding the suggestions of Twardowski '269, some patients having swan neck catheters continue to experience some tunnel infection and tunnel exit site infection. Migration of the distal portion of the catheter within the peritoneal cavity and proximal portion within the tunnel, because of ineffective anchoring of the catheter to the tissue, is believed to be the cause. Twardowski '269 and Twardowski '471 disclose porous cuffs on both the distal and proximal portions of the catheter to promote tissue ingrowth and anchoring. However, such cuffs do not fully anchor the catheter to the tissue within the patient. Due to the fatty characteristics of subcutaneous tissue, the porous cuff on the proximal portion of a swan neck catheter does not provide adequate tissue ingrowth to anchor the catheter to the subcutaneous tissue. However, it has been observed that rectus muscle tissue results in effective ingrowth into and through the porous cuff carried on the distal portion of prior art catheters.

A problem with the prior art distal portion cuffs is evident from FIG. 7 of Twardowski '471. This drawing discloses that the porous cuff on the distal portion of the catheter extends into only part of the rectus muscle. Further, the cuff passes angularly through the rectus muscle. This results in ineffective tissue ingrowth into the porous cuff in order to anchor the distal portion in the rectus muscle. Further, the distal and proximal portions of swan neck catheters are planar so that any external force exerted on the proximal portion directly dislodges the distal portion.

To enhance securement of the distal portion to the rectus muscle, the swan neck catheter of Twardowski '471 requires the use of a flange and button anchoring device which is sutured to the posterior sheath of the rectus muscle. The use of such an anchoring device not only complicates the catheter implantation procedure, but also invites necrosis of the rectus muscle tissue.

Hence, prior to the development of the present invention, a need existed for a catheter for percutaneous access to the peritoneal cavity in which distal and proximal portions of the catheter are caudally directed to eliminate tunnel infection and tunnel exit site infection. Further, a need existed for a peritoneal dialysis catheter which would securely anchor within the rectus muscle tissue without use of anchoring beads or flanges. A need also existed for a peritoneal dialysis catheter in which the distal and proximal portions of the catheter were non-planar to thereby function as a safeguard from inadvertent dislodging of the catheter from the patient.

SUMMARY OF THE INVENTION

According to the present invention, a peritoneal dialysis catheter has been developed in which distal and proximal portions of the catheter are each angularly and integrally joined to a linear connecting portion. The angular joinder of the distal and proximal portions to the connecting portion is accomplished by molding the distal and proximal portions to the connecting portion in an angle selected so that the distal portion is caudally directed within the peritoneal cavity and the proximal portion is downwardly directed along the external abdominal wall. In all embodiments of the present invention, the distal and proximal portions of the catheter are non-planar so that any external force exerted on the catheter prevents withdrawal of the catheter from the patient.

Generally, the catheter of the present invention utilizes a linear connecting portion having a length which is substantially co-extensive with the thickness of the rectus muscle. In a preferred embodiment of the present invention, a porous cuff for tissue ingrowth of the kind and type known in the art is carried on the connecting portion and preferably extends substantially the length of the connecting portion. As a result, the entire connecting portion becomes embedded in the rectus muscle upon tissue ingrowth. While the porous cuff may also be carried on the proximal portion of the catheter to promote subcutaneous tissue ingrowth, it is believed that such cuff may in some cases be eliminated.

Other advantages and aspects of the invention will become apparent upon making reference to the specification, claims, and drawings to follow.

BRIEF DESCRIPTION OF THE DRAWINGS

FIG. 1 is a front elevational view of a preferred embodiment of the catheter of the present invention;

FIG. 2 is a detailed fragmented view of a portion of FIG. 1 taken along line 2—2;

FIG. 3 is a side elevational view of FIG. 2;

FIG. 4 is a front elevational view showing implantation of the present invention in a patient;

FIG. 5 is a partial vertical section view of the fragmentary view of the catheter of FIG. 2 implanted through the abdominal wall and into the peritoneal cavity of a patient; and, FIG. 6 is a front elevational view of another embodiment of the catheter of the present invention.

DETAILED DESCRIPTION OF THE INVENTION

While this invention is susceptible of embodiment in many different forms, there is shown in the drawings and will herein be described in detail a preferred embodiment of the invention. The present disclosure is to be considered as an exemplification of the principles of the invention and is not intended to limit the broad aspect of the invention to embodiment illustrated.

Referring now to the drawings, FIG. 1 discloses a preferred embodiment of catheter 10 of the present invention comprised of flexible tubing, preferably a thermoplastic material such as polyurethane. Thermoplastic material is preferred because such material may re-form at body temperatures enabling the catheter to conform in vivo to internal body contours. Thermoset materials, such as silicone, cannot be so modified.

Catheter 10 is comprised of a distal portion 12 which, as later explained, will extend into the peritoneal cavity of the patient and a proximal portion 14. As will be later explained, a first segment 14' of proximal portion 14 passes through the subcutaneous and cutaneous tissue of a patient, whereas a second segment 14" extends externally from the patient and downwardly along the external abdominal wall of the suprapubic region of the abdomen.

Distal portion 12 includes a distal end 16 which, in a preferred embodiment, comprises a spiral or coiled configuration 18 which lies in a single plane when the catheter is in a natural, unstressed condition. Spiral 18 includes a plurality of openings 20 which permits passage of fluid such as a dialysate.

Proximal portion 14 has a proximal end 22 which may be coupled to a source of dialysate or a container for dialysate drainage. In all embodiments of the present invention, distal portion 12 and proximal portion 14 are preferably linear in configuration.

As best disclosed in FIG. 3, distal portion 12 and proximal portion 14 are linked by a linear connecting portion 24. Connecting portion 24 has a length preferably about one centimeter which is substantially co-extensive with the thickness of the rectus muscle. As a result, connecting portion 24 is substantially embedded within the rectus muscle upon implantation of catheter 10. In all embodiments of the present invention, connecting portion 24 carries about its circumference a porous cuff 26 which preferably extends the length of connecting portion 24. Cuff 26 may be made from a woven biocompatible material known in the art, such as Dacron ® or woven Tecoflex ®. Cuff 26 results in a thorough embedding and anchoring of connecting portion 24 within the rectus muscle. A porous cuff 28 may also be carried on first segment 14' of proximal portion 14, though in some instances, may be eliminated.

As best disclosed in FIGS. 2 and 3, distal portion 12 and proximal portion 14 are intrically formed with and angularly joined to connecting portion 24. Preferably, the angular joinder of distal portion 12 and proximal portion 14 to connecting portion 24 is achieved by molding bend segments 30 into catheter 10. As a result of such molding process, bend segments 30 remain in catheter 10 even when catheter 10 is in its natural unstressed condition. Angle "a" formed between the longitudinal axis of the connecting portion and longitudinal axis of distal portion 12 should be such that when catheter 10 is implanted into a patient, distal portion 12 is directed caudally into the peritoneal cavity. Likewise, angle "b" defined between the longitudinal axis of connecting portion 24 and longitudinal axis of proximal portion 14 should be such that upon implantation of catheter 10 into a patient, proximal end 22 is directed downwardly along the external abdominal wall of the patient. To assure such caudal direction of distal portion 12 and downward direction of proximal portion 14, such angles are preferably acute angles.

FIG. 2 discloses another aspect of the present invention in which distal portion 12 and proximal portion 14 are non-planar with each other. Unlike prior art peritoneal catheters in which distal and proximal catheter portions are co-planar, the present invention uses non-planar distal and proximal portions to prevent inadvertent withdrawing or dislodging the catheter from the patient. Specifically, if second segment 14' of the catheter is pulled upon, the non-planar and angular orientation of distal portion 12 will prevent withdrawal of the catheter from the patient by abutting against the inner surfaces of the peritoneal cavity. As disclosed in FIG. 2, angle "c" defines the degree of spread between distal portion 12 and proximal portion 14. Preferably, angle "c" should be an acute angle.

Finally, FIGS. 1 and 2 disclose that catheter 10 may include a longitudinal, radiopaque stripe as is known in the art for ease of x-ray confirmation of catheter position upon implantation.

FIGS. 4 and 5 disclose the orientation and positioning of catheter 10 upon implantation. In order to minimize tunnel infection and tunnel exit site infection, it is essential that distal end 16 of distal portion 12 be directed caudally within the peritoneal cavity and that proximal end 22 of proximal portion 14 also be downwardly directed along the external abdomen wall. Catheter 10 may be implanted by any technique known in the art. For example, in the "Y-Tec" method, distal portion 12 and connecting portion 24 are inserted through a surgically formed percutaneous passage into the peritoneal cavity. Next, a tunnel is formed through the subcutaneous and cutaneous tissue which exits through a second opening formed in the epidermis. As disclosed in FIG. 5, proximal portion 14 is urged through the tunnel so that first segment 14' passes through the subcutaneous and cutaneous tissue while second segment 14" is positioned external to the abdomen wall. The tunnel assures that proximal portion 14 is maintained in a downward direction.

Finally, the percutaneous passage to the peritoneal cavity is sutured closed.

FIG. 4 discloses the non-planar orientation of distal portion 12 and proximal portion 14, so that portions 12 and 14 are angularly off-set. Hence, if external force is exerted on proximal portion 14, catheter 10 will not easily be dislodged or withdrawn from the patient. In prior art catheters having co-planar distal and proximal portions, such force is imparted directly to the distal portion 12 causing dislodgement of the catheter. In the present invention, distal portion 12, by being non-planar with proximal portion 14, will merely abut against the inner surfaces of the peritoneal cavity to prevent withdrawal or dislodgement of catheter 10.

FIG. 5 discloses the significance of the configuration of connecting portion 24. As disclosed in FIG. 5, the length of connecting portion 24 is co-extensive with the thickness of rectus muscle A. Preferably, porous cuff 26 is also co-extensive with the length of connecting portion 24. Hence, connecting portion 24 is imbedded in rectus muscle tissue which, as previously mentioned, efficaciously grows into the pores of cuff 26. Bend segment 30 on distal portion 12 caudally directs distal end 16 into peritoneal cavity D. Likewise, bend segment 30 on proximal portion 14, with the assistance of a surgically formed tunnel, downwardly directs first segment 14' through subcutaneous tissue C which emerges through the epidermis. Second segment 14' emerges downwardly at an exit site E. A second porous cuff 28 may be carried on first segment 14' to permit ingrowth of subcutaneous tissue. However, in some instances, the embedding and efficacious anchoring of cuff 26 into rectus muscle A may prove sufficient.

Finally, FIG. 6 discloses another embodiment of the present invention in which distal end of the distal portion is linear, rather than comprising the spiral configuration disclosed in FIG. 4.

Preliminary clinical evaluation of the present invention revealed a virtual elimination of tunnel and tunnel site infection. Likewise, many patients are able to initiate peritoneal dialysis within days of catheter implantation with no adverse effects. It is believed that the connecting portion 24 suspends the catheter 10 within the percutaneous passage pending tissue ingrowth into the porous cuffs which provides sufficient initial securement to begin dialysis.

Preliminary clinical investigation has revealed no subsequent tunnel site or tunnel exit site infection many months after catheter implantation which indicates that upon ingrowth of rectus muscle tissue into porous cuff 26 on connecting portion 24, catheter migration is eliminated. Finally, despite the absence of any anchoring buttons or flanges such as those found in the prior art, initial observations have revealed no catheters which have become inadvertently dislodged or withdrawn.

While the specific embodiments have been illustrated and described, numerous modifications come to mind without significantly departing from the spirit of the invention and the scope of protection is only limited by the scope of the accompanying Claims.

I claim:

1. A catheter being adapted for percutaneous access to a peritoneal cavity of a patient, such as in peritoneal dialysis, comprising:
    a flexible tubular member having a distal portion adapted to be disposed within the peritoneal cavity, the distal portion having an open distal end;
    a proximal portion of the tubular member having one segment being adapted for passing through the subcutaneous and cutaneous tissues of the patient and an other segment adapted to be disposed along the external abdominal wall of the patient and terminating in a proximal end;
    a linear connecting portion between the distal portion and the proximal portion, the connecting portion adapted to be substantially disposed through the rectus muscle of the patient, the connecting portion being adapted to have a length generally co-extensive with the thickness of the rectus muscle;
    porous cuff means being carried on the connecting portion; and,
    the catheter having a preformed and unstressed configuration with the distal portion being angularly joined to the connecting portion to direct the distal end caudally within the peritoneal cavity, the proximal portion being angularly joined to the connecting portion to direct the proximal end downwardly along the external abdominal wall, the distal portion and the proximal portion being non-planar with each other.

2. The catheter described in claim 1 wherein the porous cuff means extends generally the length of the connecting portion.

3. The catheter described in claim 1 wherein the one segment of the proximal portion carries a porous cuff means.

4. The catheter described in claim 1 further including:
    a plurality of longitudinally spaced perforations positioned near the distal end, the perforations permitting fluid to be instilled and drained from the peritoneal cavity.

5. The catheter described in claim 4 wherein the distal portion near the distal end comprises a spiral configuration laying in a plane generally perpendicular to a vertical plane of the connecting portion.

6. The catheter described in claim 1 wherein the angle formed by the joinder of the distal portion and the connecting portion is an acute angle; and, the angle formed by the joinder of the proximal portion and the connecting portion is an acute angle.

7. The catheter described in claim 1 wherein the tubular member is made from a thermoplastic material.

8. The catheter described in claim 7 wherein the thermoplastic material includes polyurethane.

* * * * *

UNITED STATES PATENT AND TRADEMARK OFFICE
CERTIFICATE OF CORRECTION

PATENT NO. : 4,935,004
DATED : June 19, 1990
INVENTOR(S) : Cosme Cruz

It is certified that error appears in the above-identified patent and that said Letters Patent is hereby corrected as shown below:

In Column 4, line 7, delete "intrically" and insert therefor --integrally--.

Signed and Sealed this

Second Day of June, 1992

Attest:

DOUGLAS B. COMER

*Attesting Officer*      *Acting Commissioner of Patents and Trademarks*